US008880149B2

(12) United States Patent
Barbot et al.

(10) Patent No.: US 8,880,149 B2
(45) Date of Patent: Nov. 4, 2014

(54) LOCALIZATION OF A DEVICE FOR MR-GUIDED INTERVENTION

(71) Applicants: Julien Christian Barbot, Princeton, NJ (US); Sunil Goraksha Patil, Columbia, MD (US); Klaus J. Kirchberg, Plainsboro, NJ (US); Steven M. Shea, Baltimore, MD (US)

(72) Inventors: Julien Christian Barbot, Princeton, NJ (US); Sunil Goraksha Patil, Columbia, MD (US); Klaus J. Kirchberg, Plainsboro, NJ (US); Steven M. Shea, Baltimore, MD (US)

(73) Assignee: Siemens Aktiengesellschaft, Munich (DE)

( * ) Notice: Subject to any disclaimer, the term of this patent is extended or adjusted under 35 U.S.C. 154(b) by 22 days.

(21) Appl. No.: 13/627,171

(22) Filed: Sep. 26, 2012

(65) Prior Publication Data

US 2013/0085377 A1 Apr. 4, 2013

Related U.S. Application Data

(60) Provisional application No. 61/540,797, filed on Sep. 29, 2011.

(51) Int. Cl.
*A61B 5/06* (2006.01)
*A61B 5/055* (2006.01)
*G01R 33/28* (2006.01)

(52) U.S. Cl.
CPC ............... *A61B 5/055* (2013.01); *A61B 5/062* (2013.01); *G01R 33/287* (2013.01)
USPC ........... 600/424; 600/407; 600/421; 600/422; 600/423

(58) Field of Classification Search
CPC ................... G01R 33/285; A61B 5/06
See application file for complete search history.

(56) References Cited

U.S. PATENT DOCUMENTS

| 6,073,043 A * | 6/2000 | Schneider ...................... 600/424 |
| 2003/0120146 A1 | 6/2003 | Dumoulin |
| 2010/0210938 A1* | 8/2010 | Verard et al. .................. 600/424 |

OTHER PUBLICATIONS

C. L. Dumoulin et al., "Real-Time Position Monitoring of Invasive Devices Using Magnetic Resonance," MRM 29, pp. 411-415. 1993.
J. Barbot et al., "Accurate Localization of Active Devices During Interventional MR Imaging," Annual Meeting of the ISMRM 2011, p. 1747, May 2011.
J. Canny "A Computational Approach to Edge Detection," IEEE Transactions on Pattern Analysis and Machine Intelligence, vol. 8, pp. 679-698, Nov. 1986.
S. Mallat et al., "Characterization of Signals from Multiscale Edges," IEEE Transactions on Pattern Analysis and Machine Intelligence, vol. 14, pp. 710-732, 1992.
U.S. Appl. No. 13/226,821, filed Sep. 7, 2011.

* cited by examiner

*Primary Examiner* — Mark Remaly

(57) ABSTRACT

Localization of a coil is provided for magnetic resonance (MR)-guided intervention. A multi-scale decomposition and characteristic transitions in the power spectra for the coil are used to determine a distribution of likelihood of the coil being at each of various locations and/or to determine a confidence in the position determination. For example, the power spectra along each axis is used to generate a likelihood distribution of the location of the coil. The power spectra are decomposited at different scales. For each scale, the modulus maxima reflecting transitions in the power spectra are matched using various criteria. A likelihood is calculated for each of the matched candidates from characterizations of the matched candidates. The likelihood distribution is determined from a combination of the likelihoods from the various scales.

21 Claims, 7 Drawing Sheets

US 8,880,149 B2

LOCALIZATION OF A DEVICE FOR MR-GUIDED INTERVENTION

RELATED APPLICATIONS

The present patent document claims the benefit of the filing date under 35 U.S.C. §119(e) of Provisional U.S. Patent Application Ser. No. 61/540,797, filed Sep. 29, 2011, which is hereby incorporated by reference.

BACKGROUND

The present embodiments relate to magnetic resonance (MR) guided intervention.

The position of the catheter(s), other medical devices, or features may be determined in medical imaging. Such tracking or position detection may be used in many applications, such as visual surveillance and real-time image guided interventions. However, due to complexity of the application environments, there is possibility that the detection in the images may be inaccurate.

In interventional magnetic resonance imaging (MRI), tracking of the interventional devices is performed by utilizing locally sensitive small RF coils mounted at particular positions along the device. The localization of the coil is achieved in a few milliseconds by acquiring one dimensional (1D) projections along all three spatial directions (X, Y and Z), and, then, finding the peak or maxima in the power spectra, whose frequency is indicative of the coil position in actual space. Due to interventional device geometry, solenoid coils are utilized for this purpose. For solenoid coils, magnetic resonance (MR) signal contribution is from surrounding tissues, not the device itself. Thus, the location associated with the maximum observed in the power spectra is offset from the actual coil position by a few millimeters. In addition, the width of the peak signal may be about 3-5 mm, which leads to further ambiguity in the detected maxima position.

BRIEF SUMMARY

By way of introduction, the preferred embodiments described below include methods, systems, and computer readable storage media for localization of a coil for magnetic resonance (MR)-guided intervention. A multi-scale decomposition and the characteristic sharp transitions from the power spectra for the coil are used to determine a distribution of likelihood of the coil being at each of various locations and/or to determine a confidence in the position determination. For example, the power spectra along each axis are used to generate a likelihood distribution of the possible locations of the coil. The power spectra are decomposited at different scales. For each scale, modulus maxima reflecting sharp transitions in the power spectra are matched using various criteria. A likelihood is calculated for each of the matched candidates from characterizations of the matched candidates. The likelihood distribution is determined from a combination of the likelihoods from the various scales.

In a first aspect, a system is provided for localization of a coil for magnetic resonance (MR)-guided intervention. A medical device is operable to be positioned within a patient. The coil connects with the medical device. An MR receiver connects with the coil. A processor connects with the MR receiver. The processor is configured to calculate X, Y, and Z data from information from the coil received in response to MR pulses, the X, Y, and Z data representing intensity as a function of spatial location along X, Y, and Z axes, respectively. The processor is configured to decompose the X, Y, and Z data into multiple scales and detect a position of the coil as a function of the decomposition and at least two transitions in the intensity in each of the X, Y, and Z axes.

In a second aspect, a method is provided for localization of a coil for magnetic resonance (MR)-guided intervention. A coil in a patient and connected to an interventional device acquires projections along three spatial axes. A power spectrum is calculated for each of the projections. The power spectra are subjected to wavelet transformation. A likelihood distribution is estimated from results of the wavelet transforming. A position of the coil is detected as a function of the likelihood distribution.

In a third aspect, a non-transitory computer readable storage medium has stored therein data representing instructions executable by a programmed processor for localization of a coil for magnetic resonance (MR)-guided intervention. The storage medium includes instructions for calculating a likelihood distribution of positions of the coil, determining a coil position from the likelihood distribution, and outputting a confidence for the coil position.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

The three-dimensional position of a RF coil is determined. The RF coil is placed on an interventional device, such as a catheter, guide wire, or needle. In one approach, the coil position is determined from a maximum of the power spectrum. In an improved approach, the position is determined with higher accuracy by 1) theoretically calculating spectra models corresponding to the expected one-dimensional projection signals along three spatial axes (X, Y and Z) based on a given coil and 2) determining the probabilistic similarity (e.g., cross-correlation) of the model with the spectra of the acquired projection signal in real-time. This method relies on hardware characteristics of the coil and is sensitive to noise. In addition, outcomes of these two approaches are point estimates and do not include the degree of reliability, confidence interval, or likelihood.

Position may be determined without reliance the specific coil and with greater independence from noise. The signal of interest is treated as a singularity smoothed by a diffusion process, so a wavelet transformation is applied. Parameter estimation is then done by performing edge detection at different scales. The detected edges are characterized to find suitable patterns for a given projection signal. The resulting patterns from different scales are combined in order to estimate the parameter likelihood at every position.

Figure 1:
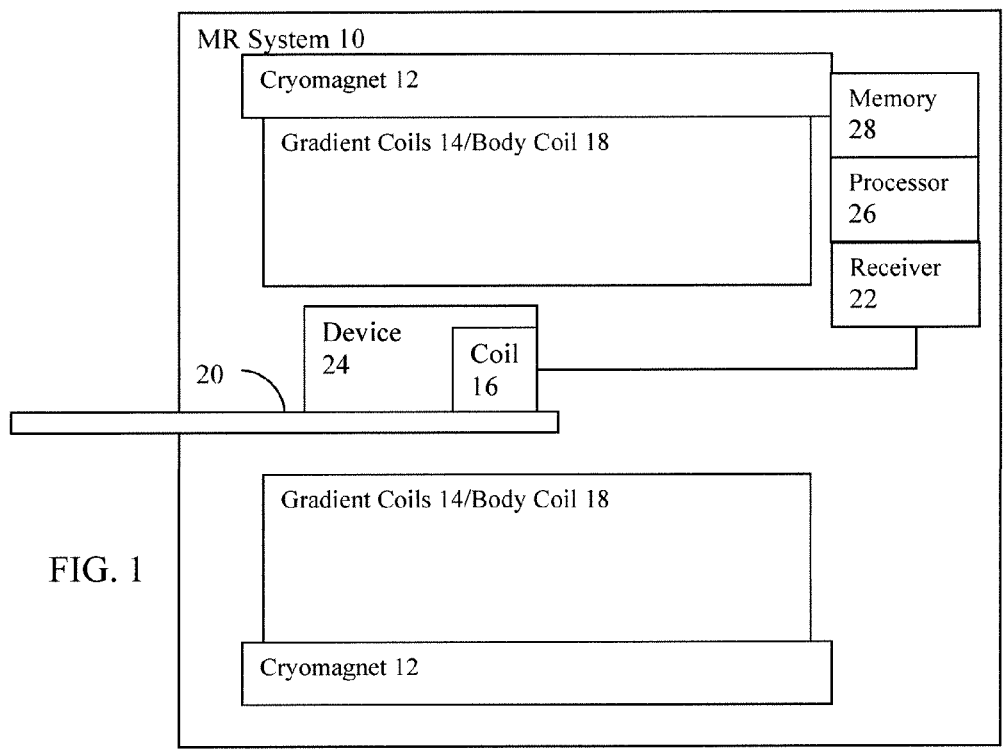
FIG. 1 is a block diagram of one embodiment of an MR system with a local coil for intervention.

FIG. 1 shows a system 10 for localization of a coil 16 for magnetic resonance (MR)-guided intervention. The system 10 includes a cryomagnet 12, gradient coils 14, whole body coil 18, local coil 16, patient bed 20, MR receiver 22, processor 26, memory 28, and intervention device 24. Additional, different, or fewer components may be provided. For example, another local coil or surface coil is provided for signal reception other than the local coil 16. In the embodiments herein, the local coil 16 is described for identifying the position of some device, but the local coil 16 and/or other local coils may be used for MR imaging.

Other parts of the MR system are provided within a same housing, within a same room (e.g., within the radio frequency cabin), within a same facility, or connected remotely. The other parts of the MR portion may include local coils, cooling systems, pulse generation systems, image processing systems, and user interface systems. Any now known or later developed MR imaging system may be used with the modifications discussed herein. The location of the different components of the MR system is within or outside the RF cabin, such as the image processing, tomography, power generation, and user interface components being outside the RF cabin. Power cables, cooling lines, and communication cables connect the pulse generation, magnet control, and detection systems within the RF cabin with the components outside the RF cabin through a filter plate.

The processor 26 and memory 28 are part of a medical imaging system, such as the MR system. In one embodiment, the processor 26 and memory 28 are part of the MR receiver 22. Alternatively, the processor 26 and memory 28 are part of an archival and/or image processing system, such as associated with a medical records database workstation or server. In other embodiments, the processor 26 and memory 28 are a personal computer, such as desktop or laptop, a workstation, a server, a network, or combinations thereof. The processor 26 and memory 28 may be provided without other components for implementing the method.

The cryomagnet 12, gradient coils 14, and body coil 18 are in the RF cabin, such as a room isolated by a Faraday cage. A tubular or laterally open examination subject bore encloses a field of view. A more open arrangement may be provided. The patient bed 20 (e.g., a patient gurney or table) supports an examination subject such as, for example, a patient with a local coil arrangement, including the coil 16. The patient bed 20 may be moved into the examination subject bore in order to generate images of the patient. In one embodiment, the local coil 16 for determining position is placed within the patient. Received signals may be transmitted by the local coil arrangement to the MR receiver 22 via, for example, coaxial cable or radio link (e.g., via antennas) for localization.

In order to examine the patient, different magnetic fields are temporally and spatially coordinated with one another for application to the patient. The cyromagnet 12 generates a strong static main magnetic field $B_0$ in the range of, for example, 0.2 Tesla to 3 Tesla or more. The main magnetic field $B_0$ is approximately homogeneous in the field of view.

The nuclear spins of atomic nuclei of the patient are excited via magnetic radio-frequency excitation pulses that are transmitted via a radio-frequency antenna, shown in FIG. 1 in simplified form as a whole body coil 18, and/or possibly a local coil arrangement. Radio-frequency excitation pulses are generated, for example, by a pulse generation unit controlled by a pulse sequence control unit. After being amplified using a radio-frequency amplifier, the radio-frequency excitation pulses are routed to the body coil 18 and/or local coils. The body coil 18 is a single-part or includes multiple coils. The signals are at a given frequency band. For example, the MR frequency for a 3 Tesla system is about 123 MHz+/−500 KHz. Different center frequencies and/or bandwidths may be used.

The gradient coils 14 radiate magnetic gradient fields in the course of a measurement in order to produce selective layer excitation and for spatial encoding of the measurement signal. The gradient coils 14 are controlled by a gradient coil control unit that, like the pulse generation unit, is connected to the pulse sequence control unit.

The signals emitted by the excited nuclear spins are received by the local coil 16. In some MR tomography procedures, images having a high signal-to-noise ratio (SNR) may be recorded using local coil arrangements (e.g., loops, local coils). The local coil arrangements (e.g., antenna systems) are disposed in the immediate vicinity of the examination subject on (anterior), under (posterior), or in the patient. The received signals are amplified by associated radio-frequency preamplifiers, transmitted in analog or digitized form, and processed further and digitized by the MR receiver 22. The recorded measured data is stored in digitized form as complex numeric values in a k-space matrix. An associated MR image of the examination subject may be reconstructed using a one or multidimensional Fourier transform from the k-space matrix populated with values. For position determination, the reconstructed data may be used without or in addition to generating an image.

In the course of an MR measurement, the excited nuclei induce a voltage in the local coil 16. The induced voltage is amplified by a low-noise preamplifier (e.g., LNA, preamp) and forwarded to the MR receiver 22.

The intervention device 24 is a medical device for positioning within a patient. The intervention device 24 is positioned in an orifice of the patient, such as through the mouth and into the esophagus. Alternatively, the intervention device 24 is positioned by surgical insertion through the skin of the patient, such as for minimally invasive surgery. In other embodiments, the intervention device 24 is inserted in an opening created as part of surgery, such as on an interpretive probe.

The intervention device 24 is a catheter, intercavity probe, needle, guide wire, or other medical device. In one embodiment, the intervention device 24 is any now known or later developed catheter for intervention or other use within a patient. The catheter is sized and shaped for use in the circulatory system, such as having a diameter of 10 French or less, but a length of a foot or more. Alternatively, the catheter is sized and shaped for use at other locations in the body. The catheter is adapted for insertion within the patient, such as through a vessel or vein for extending into a heart chamber, body cavity, or other location within the patient. The catheter may include guide wires or be inserted through another previously positioned guide catheter. The catheter may include an electrode, scalpel, balloon, stent, imaging array, tube for injection, or other device for treatment of the patient.

The local coil 16 is conductive. For example, the local coil 16 is copper. The local coil 16 is used as a receive antenna.

Any size coil 16 may be used, such as less than 4 mm in any direction. The coil 16 may be larger. Due to placement on a catheter, smaller coils 16 may be desired. For example, the coil is about 1 mm in diameter and height. Non-symmetric size may be provided.

Figure 2:
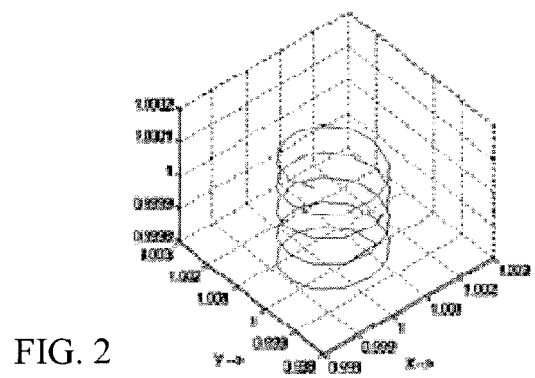
FIG. 2 is a graphical representation of one embodiment of a simulated solenoid coil.

The coil 16 is a solenoid coil. FIG. 2 shows an example of a solenoid coil. The coil 16 has a helical arrangement. Other coil geometries may be used, such as a planar coil.

The coil 16 connects with the intervention device 24. The connection with the intervention device 24 may be a connection on the outside, placement within, or otherwise formed as part of the intervention device 24. In one embodiment, the coil 16 is positioned within an outer covering of a tip of a catheter. Other coils 16 may be positioned at other locations on the catheter, such as every 5 mm or so along a portion of the catheter.

The MR receiver 22 connects with the coil 16. The connection is wired (e.g., coaxial cable) or wireless. The connection is for data from the coil 16 to be transmitted to and received by the MR receiver 22. The data is K-space data. In response to an MR pulse, the coil 16 receives the K-space data and transmits the data to the MR receiver 22. Any pulse sequence may be used, such as a simple pulse sequence acquiring projections along three spatial axes. Any spatial resolution may be provided, such as a spatial resolution of 0.78 mm.

The MR receiver 22 includes the processor 26 or another processor (e.g., digital signal processor, field programmable gate array, or application specific circuit for applying an inverse Fourier transform) for reconstructing the K-space data. The MR receiver 22 is configured by hardware or software to calculate X, Y, and Z projection data from the K-space data from the coil 16. Other transforms for reconstructing spatial data from the K-space data may be used.

The processor 26 applies an inverse Fast Fourier transform to calculate the power spectrum of the projection data. The power spectrum provides intensity as a function of frequency. The frequency corresponds to space or distance. The MR data as acquired is a function of frequency and after applying inverse FT becomes a function of space.

The spectrum for each axis is responsive to the location of the coil 16 relative to the gradient coils 14. By obtaining projection data from three orthogonal axes, the location in three-dimensions may be represented. Projection data representing intensity as a function of frequency, and thus spatial location, along X, Y, and Z axes is acquired. In other embodiments, one or two-dimensional location is used.

The MR receiver 22 or the processor 26 may pre-process the spectra. For example, the spectra are low pass filtered. As another example, each spectrum is up-sampled or decimated.

Figure 3A:
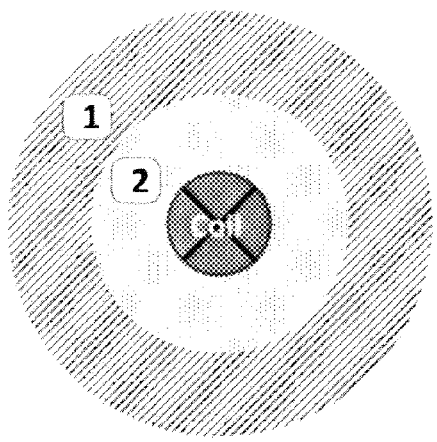
FIG. 3A shows example anatomy around a coil within a patient.
Figure 3B:
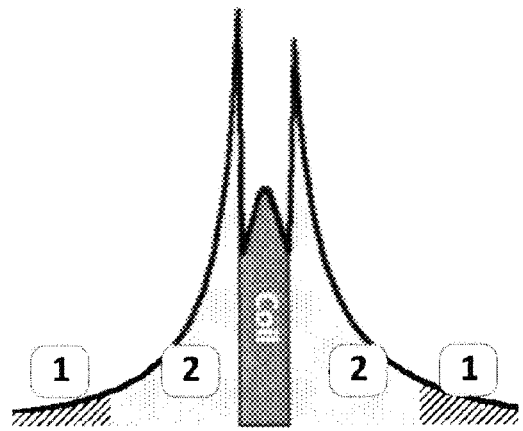
FIG. 3B shows an example spatial signal relative to the anatomy and coil.

The spectra are responsive to the anatomy around the coil 16. FIG. 3A shows example anatomy as including tissue, such as a vessel or organ wall with fluid on an interior. The coil is positioned within the fluid, surrounded by the tissue. Other positioning and/or anatomy may be provided. FIG. 3B shows an example theoretical signal pattern formed by the coil and surrounding anatomy. The signal contributions from the surrounding anatomy form variations of different sharpness. These variations or edges are features that may be detected with a pattern detection algorithm. For example, the sharp transitions (i.e., singularities) associated with the interface from the fluid to the coil are edges that may be detected. Edges may be noise-robust features. In a noisy environment, detect of edges may be performed where finer features may not be consistently detectable. Patterns formed by edges are similar enough across different devices so that the algorithm supports different hardware.

The processor 26 detects the edges in order to calculate a likelihood distribution of the position of the coil 16. The processor 26 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for determining position. The processor 26 is a single device or multiple devices operating in serial, parallel, or separately. The processor 26 may be a main processor of a computer, such as a laptop or desktop computer, or may be a processor for handling some tasks in a larger system, such as being part of the MR receiver 22 or MR imaging system 10. The processor 26 is configured by instructions, design, hardware, and/or software to perform the acts discussed herein, such as determination of position of the local coil 16.

The processor 26 connects with the MR receiver 22 to receive the power spectrum data. The processor 26 detects the likely location of the coil from the power spectrum data in a noise robust process. The likely location is detected from a distribution of likelihood over a plurality of possible locations. Edge detectors are based on matching a signal with specific edge patterns, such as using convolution with a mask. Example edge detectors include sobel and laplacian operators. However, noise influence on such operators is dramatic. For a more noise robust process, the processor 26 is configured to implement the calculations shown in FIG. 4 using likelihood distribution and/or multiple scales.

Figure 4:
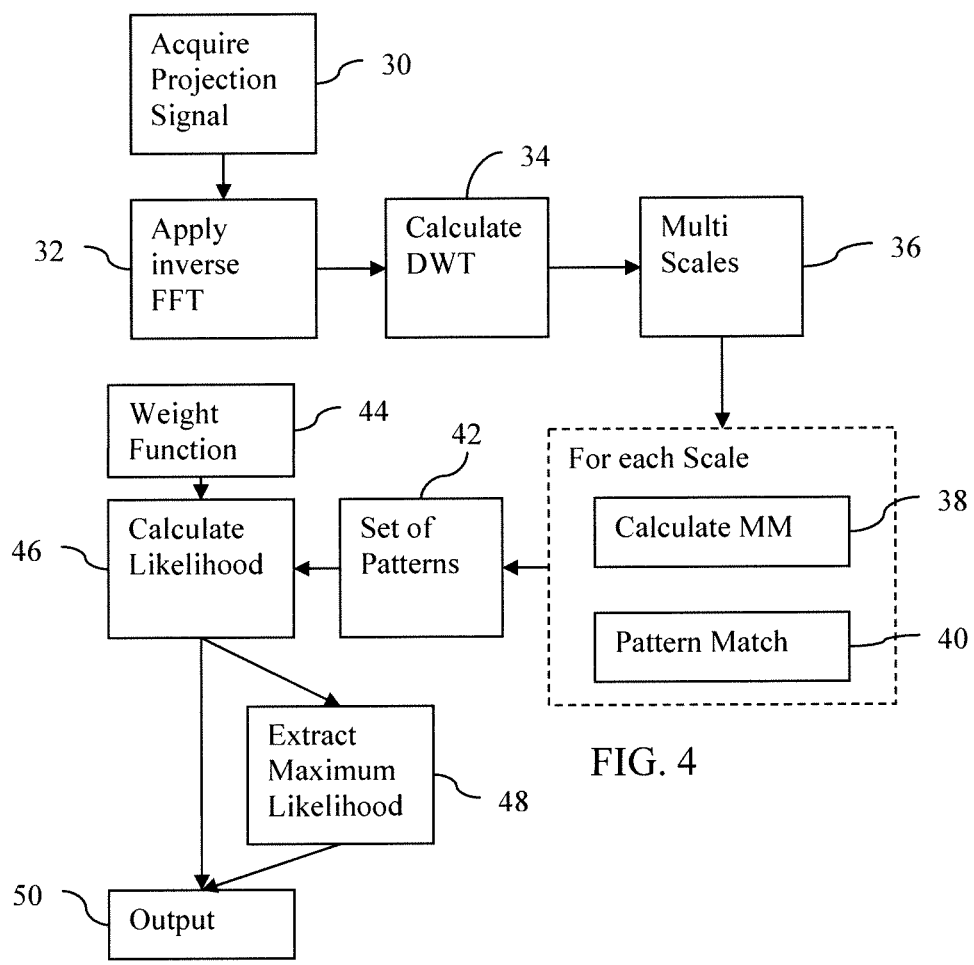
FIG. 4 is a graphical illustration of actions performed by a configured processor for localizing a coil for magnetic resonance-guided intervention.

One example of using multi-scale decomposition to determine a likelihood distribution of location is shown in FIG. 4. Confidence in the likeliest position or the position in general may be determined from the likelihood distribution. The detection uses pairs of edges or transitions, such as associated with the sharp transition occurring on both sides of the coil 16 along any direction.

In general, the processor 26 performs the processes of multi-scale decomposition in process 34. The signal is transformed into different basis with wavelet transform. The processor 26 uses the multi-scale decomposition to calculate modulus maxima at each scale in process 38. Edge detection and characterization is performed in process 40 based on the modulus maxima in each scale. Patterns associated with the modulus maxima are used at each scale. The processor 26 calculates parameter likelihood in process 46 by combining matching patterns of modulus maxima. The parameter likelihood from the different matched modulus maxima are combined in process 48, providing a likelihood distribution. The processor 26 may extract the maximum of likelihood to obtain the final estimation of position, leading to a robust and device independent parameter estimation including confidence and likelihood information. Other approaches than used in FIG. 4 to determine likelihood distribution, confidence, or position may be used. For example, multi-scale decomposition is not used. Other multi-scale decomposition approaches than used in FIG. 4 may be provided.

In FIG. 4, the projection signal is acquired in process 30 as discussed above using the MR receiver 22. In process 32, the inverse FFT is applied by the MR receiver 22 or the processor 26 to provide the signal from the coil 16 in one or more directions as a function of space. For example, the signal represented in FIG. 3B is acquired. For three-dimensional position, data along three axes, X, Y, and Z data, is calculated from the information from the coil 16 received in response to MR pulses. After the inverse FFT, the X, Y, and Z data represents intensity as a function of spatial location along the X, Y, and Z axes, respectively.

In process 34, the processor 26 is configured to decompose each of the X, Y, and Z data into multiple scales. The X, Y, and Z data are processed separately to estimate position along the X, Y, and Z axes independently. The discussion below for the processes of FIG. 4 is directed to the X axis, but is applied to or repeated for each axis to find position in three-dimensions.

Different scales have different accuracy. Greater smoothing at some scales removes noise, but may also remove actual signal. The loss of accuracy for some scales may be offset by an increase in confidence. For scales with less smoothing, greater accuracy may be provided, but with more noise. By performing analysis at different scales, the benefits of both accuracy and confidence may be provided.

Any decomposition may be used. A canny operator detects edges using a multi-scale analysis, which may minimize multiple responses to a single edge. The signal is convoluted with a smoothing function in order to reduce the noise susceptibility. The first order derivative of a Gaussian or other smoothing function may be used.

In one embodiment, the decomposition uses a wavelet transform. Any wavelet transform of the signal into two or more scales may be used. Multi-scale edge detection algorithms are related to wavelet transforms. Multi-scale edge detectors smooth the signal at various scales and detect sharp variations points from their first or second order derivatives. The extreme of the first derivative correspond to the zero-crossings of the second derivative and to the inflection points of the smoothed signal.

The transform isolates edge information by smoothing at different scales. A smoothing function is any function $\theta(x)$ twice differentiable with $\int \theta(x)dx=1$ and that converges to 0. Defining $\psi^a(x)$ and $\psi^b(x)$ as first and second order derivatives of $\theta(x)$ provides:

$$\psi^a(x)=d\theta(x)/dx \text{ and } \psi^b(x)=d^2\theta(x)/dx^2 \qquad (1)$$

The functions $\psi^a(x)$ and $\psi^b(x)$ may be considered wavelets as their integral is equal to 0. The wavelet transform at the scale s and position x, computed with respect of wavelet $\psi$ is defined by:

$$W_s f(x)=f*\psi_s(x) \qquad (2)$$

For the first and second order derivatives:

$$W_s^a \Box f(x) = f * \left( s \frac{d\theta_s}{dx} \right)(x) = s \frac{d}{dx}(f*\theta_s)(x) \qquad (3)$$

$$W_s^b \Box f(x) = f * \left( s \frac{d^2\theta_s}{dx^2} \right)(x) = s \frac{d^2}{dx^2}(f*\theta_s)(x) \qquad (4)$$

$W_s^a f(x)$ and $W_s^b f(x)$ are, respectively, the first and second order derivative of the signal smoothed at the scale s. The derivatives highlight the possible edge or transitions. The local extrema of $W_s^a f(x)$ correspond to the zero crossing of $W_s^b f(x)$ and the inflection points of $f*\theta_s(x)$. In the particular case where $\theta(x)$ is a Gaussian, the extrema detection corresponds to a Canny edge detection. Other functions than Gaussian may be used.

Any number of scales and corresponding sampling of scales may be used. A continuous scale may require excessive processing. Instead, the scale is limited. For example, a dyadic wavelet transform is used as a scale parameter, s. For fast numerical implementations, it is possible that the scale varies only along dyadic scales $(2^j) j \in z$. The wavelet $\psi(x)$ is denoted at scale $2^j$ as $\psi_{2^j}(x)$. The wavelet transform of f(x) at the scale $2^j$ then becomes:

$$W_{2^j}f(x)=f*\psi_{2^j}(x) \qquad (5)$$

Figure 5:
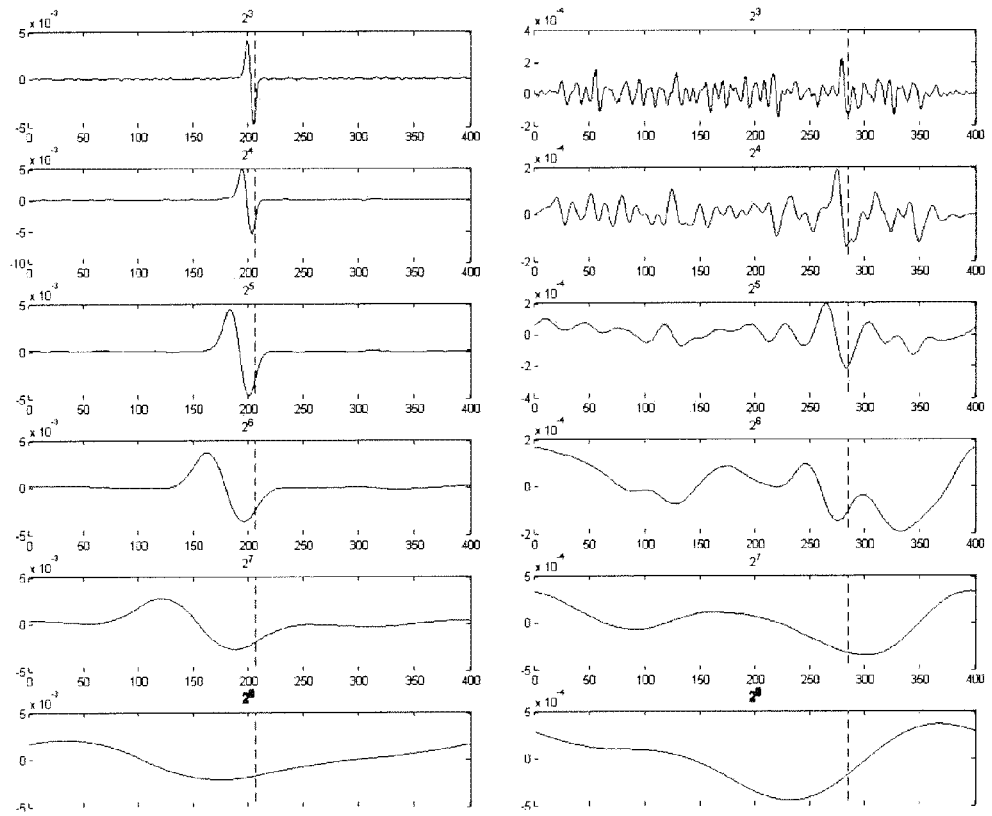
FIG. 5 illustrates multi-scale wavelets of a return from a coil in high and low signal-to-noise situations.

As a result of the multi-scale decomposition, a plurality of signals at different scales is provided as represented at 36. FIG. 5 shows two examples of a signal at different scales produced using a dyadic wavelet transform with a Gaussian function. Six different dyadic scales ($s=2^j; j \in 3 \ldots 8$) are used. On the left side of FIG. 5, a signal with high signal-to-noise ratio is shown. A multi-scale decomposition of a more realistic low signal-to-noise ratio signal is shown on the right side. As represented by the multi-scale signals for the low signal-to-noise ratio, multiple transitions are found where only two transitions represent the actual position of the coil 16.

The transitions or edges more likely to be the actual edges are determined for each scale. Since the actual position includes two edges as a characteristic of the coil, pairs of possible edges and characteristics of the pairs are used to select one or more edges in each scale.

In the process 38, the processor 26 calculates at least one modulus maximum for each of the multiple scales. To characterize the multi-scale information, local extrema are determined. Where $W_s f(x)$ is the wavelet transform of f(x), then the local extrema is any point $(s_0, x_0)$ such that $\partial (Wf(s_0,x))/\partial x$ has a zero-crossing at $x=x_0$. The modulus maxima is any local extrema point $(s_0, x_0)$ such that $|Wf(s_0,x)|<|Wf(s_0,x_0)|$. The modulus maxima are any local extrema where the signal at adjacent locations is below $x_0$.

Figure 6:
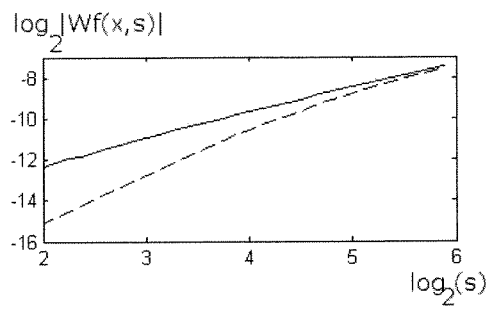
FIG. 6 illustrates decay of modulus maxima across scale.

As shown in FIG. 6, edge smoothness may be further characterized by estimating the decay of the wavelet maxima across scales. The high signal-to-noise ratio transforms are used to map the decay. FIG. 6 shows the decay as a function of $\log_2$.

Figure 7:
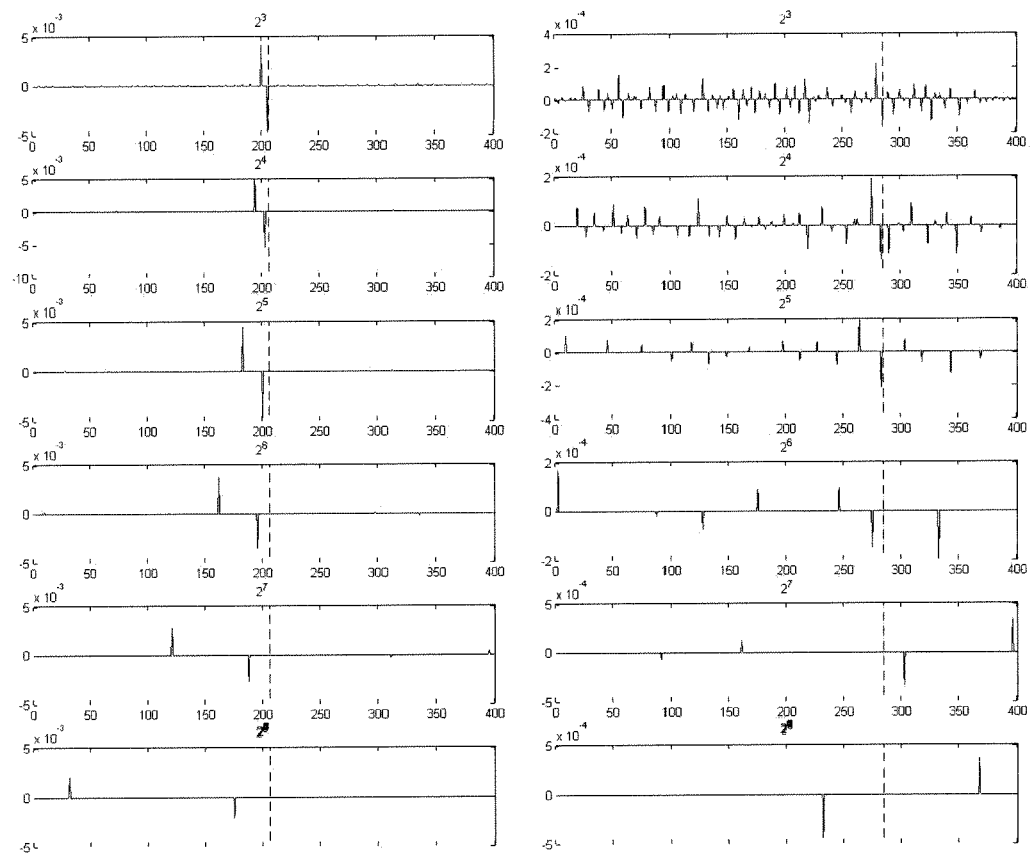
FIG. 7 illustrates modulus maxima for the wavelets of FIG. 5.

FIG. 7 shows the modulus maxima identified by the processor 26. The examples of FIG. 7 are the modulus maxima from the dyadic wavelet transforms and at the scales shown in FIG. 5. In particular, the modulus maxima of the projection signal are shown at the six different dyadic scales. The left side shows the modulus maxima for the high signal-to-noise ratio transforms, and the right side shows the modulus maxima for the low signal-to-noise ratio transforms. For the signal with high SNR, there is a convergence towards the actual coil position. While it becomes more challenging for the low SNR signal, some consistency across different scales occurs where the coil 16 is present.

Using the modulus maxima, many edges may be detected in one or more scales. Some of the edges are not likely to be the actual edges. Candidate or possible edges of interest or actual edges for the coil 16 are identified using characterization of the modulus maxima and patterns associated with the characteristics in process 40. Since each coil 16 is associated with two edges, pairs of the transitions are detected using the patterns. More than one pair may be detected at any given scale, but some edges are ruled out.

To define a pattern for the signal of interest, one or more properties are used. These characterizations are based on the detected edges as provided by the modulus maxima. These characterizations discriminate between edges originating from noise and edges from the projection signal (i.e., due to the actual coil).

Figure 8:
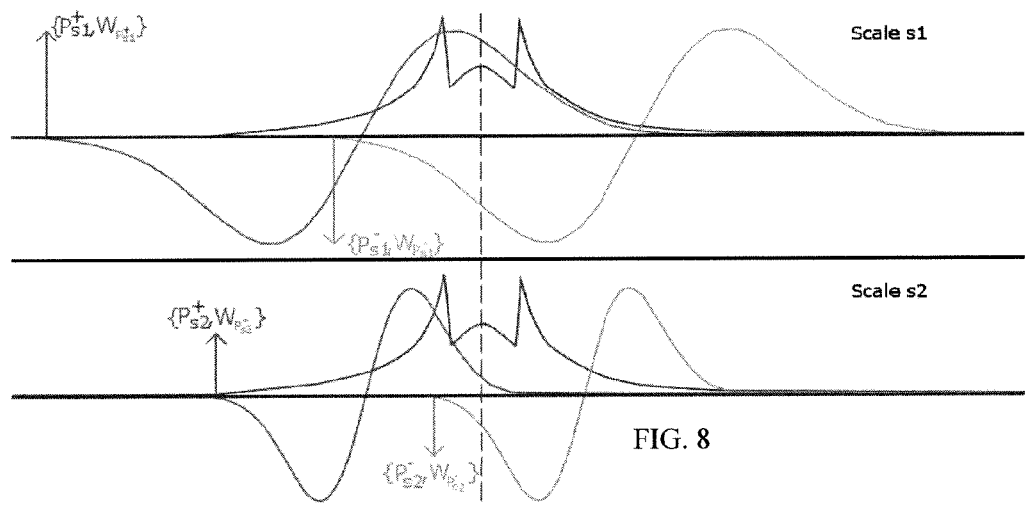
FIG. 8 illustrates a model of simulated modulus maxima at two different scales.

FIG. 8 shows a model simulation of modulus maxima results at two different arbitrary scales, s1 and s2. A model of the signal as a function of space is laid over the wavelet positioned at the modulus maxima at each scale. $(P_s^+, W_s^+)$ and $(P_s^-, W_s^-)$ are the modulus maxima positions P and magnitude W for positive and negative edges, respectively. The actual coil position is represented by the dashed, vertical line. The amount of shift from the position P to the actual coil position is different for each scale. The direction of the shift is the same. The magnitude W for the positive and negative modulus maxima is the same.

The characteristics shown in FIGS. 6 and 8 provide a pattern. The patterns are used to detect candidates for the coil position at each scale. Three characteristics are the signal symmetry of the magnitude of matching positive and negative modulus maxima, a distance of shift being proportional to the scale, and the decay of the magnitude over scale. The signal symmetry is represented as $W_s^+ + W_s^- = 0$. The distance $P_s^- - P_s^+$ is proportional to the scale s. With only the dyadic scale j, $P_s^- - P_s^+ = c2^{j-1}$, where c is a constant that depends on the signal. The constant is based on the sharpness of the edge, such as a maximum convolution or overlap of the derivative of the signal and the modulus maxima. The modulus maxima amplitude or decay across scales is represented as $|W^{+-}|$. This property depends on the signal of interest and the scale as shown in FIG. 6. The decay may be calculated empirically as an estimated function f(s) so that $|W^{+-}| = f(s)$. For example, the decay value is calculated using good or high signal-to-noise ratio. FIG. 6 represents one such empirical calculation. This decay may be matched to the possible edges across scales to identify a matching pattern of possible edges.

These three characteristics are used by the processor 26 to detect pairs of edges or modulus maxima that fit the pattern of characteristics. Because these characteristics are affected by noise and vary among themselves, the detection may be thresholded based on empirical values. Acceptable ranges for each characteristic and/or combinations of characteristics are empirically determined and applied to the possible combinations of edges in each scale. Any pairs of modulus maxima with the desired characteristics are identified. The resulting pairs are then considered as candidates for the pattern. Other patterns of characteristics and/or characteristics may be used.

Figure 9:
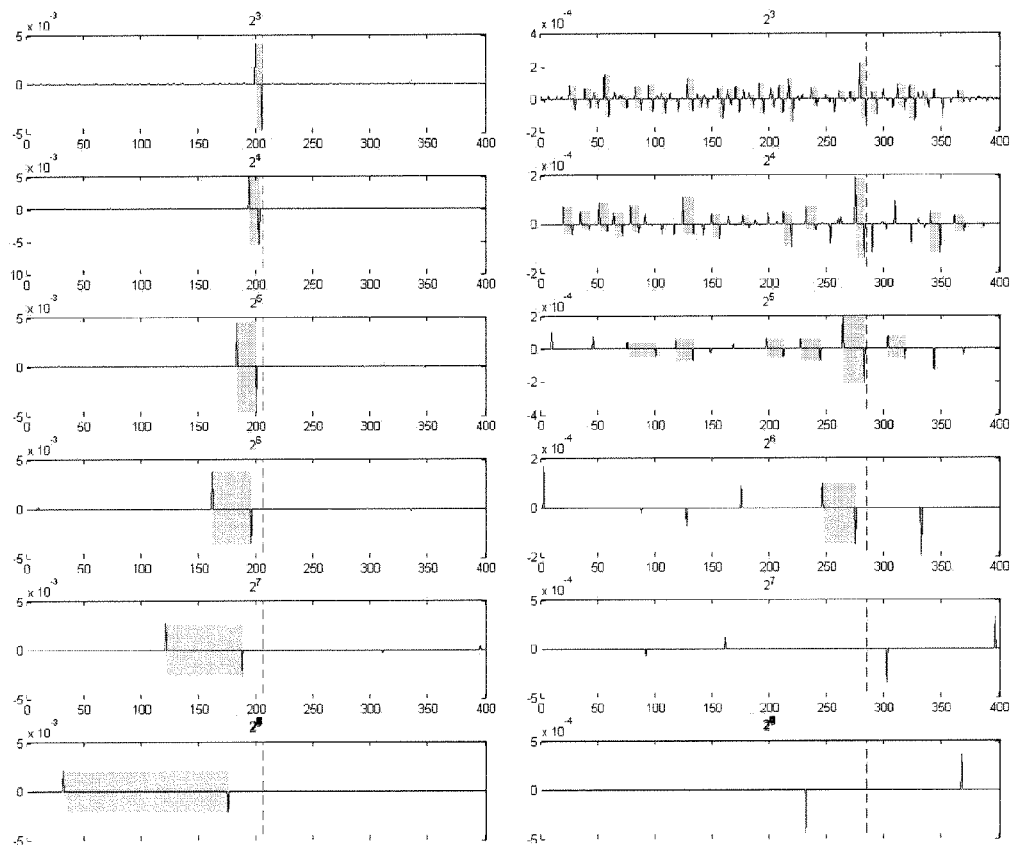
FIG. 9 illustrates pairing of modulus maxima of FIG. 7 using pattern detection.

FIG. 9 shows identified pairs at each scale. The pairs of positive and negative modulus maxima satisfying the pattern of characteristics are shown with grey blocks connecting them. The confidence intervals for the modulus maxima signals of FIG. 7 satisfying the pattern of characteristics are shown as well. The grey represents the confidence intervals. The modulus maxima not connected by grey blocks are ruled out or are not candidates as these maxima do not satisfy the pattern. In FIG. 4, the set satisfying the patterns are shown at 42. The detected modulus maxima positions are shifted proportionally to the scale since the starting point of the wavelet is used for detection. The middle point of the wavelet is the desired position. The middle point is denoted as $P_s^{+/-*}$.

For the low SNR signal, there are still false positives even among the pairs satisfying the pattern. Further processing is used to discriminate between the remaining modulus maxima. Rather than rule out the false positives, likelihood is used to determine the position. In process 46, the processor 26 estimates a parameter likelihood for detecting the position. The parameter likelihood is estimated for each candidate pair of the set 42.

Any estimation of likelihood may be used. The estimation represents a distribution of position likelihood associated with the pair. In one embodiment, a Gaussian kernel is generated for every detected pair $P_s^+, P_s^-$. The kernel is defined by the Gaussian and any weighting for multiple candidates in one scale. One or more Gaussian distributions are generated for each scale. The Gaussian has a distribution given by:

$$\mu = (P_s^+ + P_s^-)/2 \text{ and } \sigma = 2^s.$$

Where there is more than one candidate pair in a given scale, the parameter likelihood is estimated for each. The likelihood associated with any given pair is weighted to account for the distribution of likelihood among multiple pairs. The distribution of likelihood for the scale is distributed among the candidate pairs. Any criteria may be used for the distribution. For example, the parameter likelihood for multiple pairs of the transitions at a same scale is divided as a function of a number of the pairs at the same scale, an amplitude of modulus maxima for the pairs, and a symmetry of the transitions of each pair. Since the pair has a same or similar amplitude to meet the pattern, the same or similar amplitude is used. Using u for up and d for down (+/−), the amplitude of the modulus maxima is $|W_s f(x_u)|$ or $|W_s f(x_d)|$. Any symmetry function may be used, such as $1 - |(W_s f(x_u) + W_s f(x_d))|$. Additional, different or fewer criteria may be used.

The Gaussian distribution for each pair is determined and positioned relative to the pair. The criteria are used to weight the variance and/or amplitude of each pair's Gaussian distribution. Any weighting function may be used. The weighting function is represented at 44 in FIG. 4. In one embodiment, the criteria are used as input values to a look-up table and variance and/or amplitude weights are output. In other embodiments, an equation provides the weights with the criteria as variables. The equation and/or look-up table may be empirically determined. The total weight for the variance is unity, and the total weight for the amplitude is unity. The weights are applied to the variance, amplitude, or variables to calculate variance and/or amplitude.

The kernel variance and amplitude depends on the number of detected patterns at that scale and the scale itself. At large scales, the kernels have high variance and confidence as signal smoothed at large scale are less affected by noise but also less accurate. At lower scales, the kernels have a low variance and low confidence as detection at smaller scales are localized but easily trigger false positives due to noise.

Figure 10A:
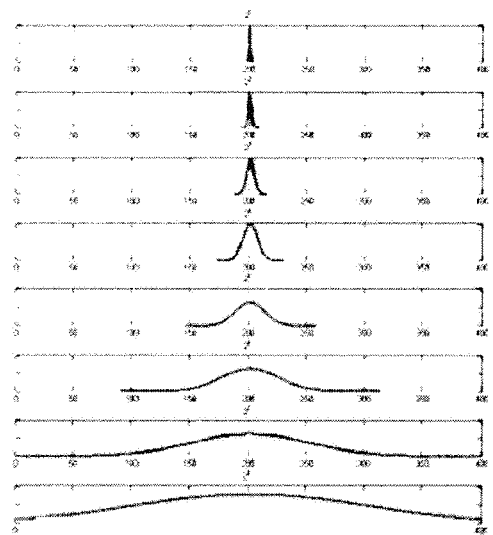
FIGS. 10A and B illustrate example likelihoods determined from pairs of modulus maxima in low and high noise environments.
Figure 10B:
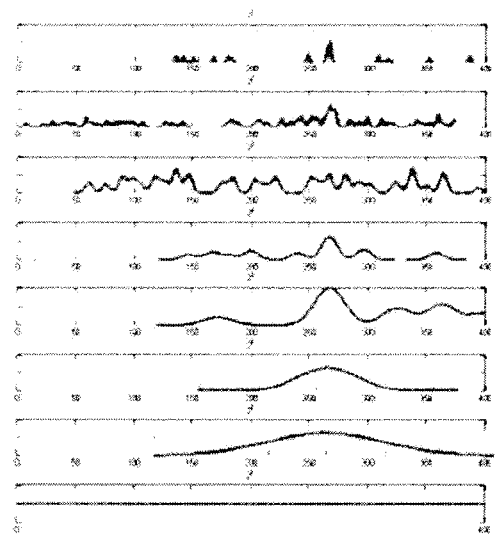

FIGS. 10A and B show parameter likelihood for high and low signal-to-noise ratio examples. The high signal-to-noise ratio example of FIG. 10A has a single pair for each scale. As a result, the Gaussian distribution of likelihood is a single Gaussian curve based on the position and scale. The low signal-to-noise ratio example of FIG. 10B has multiple candidates in the first five scales and no candidate in the eighth scale, $(s = 2^j; j \in 1 \ldots 8)$. For multiple candidates, the Gaussian curves blend or connect together. The relative variance and amplitude for each are based on the weighting.

Figure 11A:
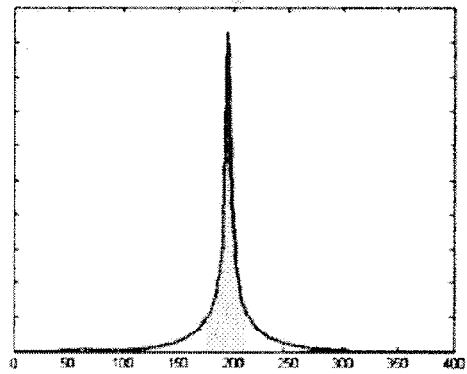
FIGS. 11A and B illustrate example likelihood distributions of coil position combined from different scales illustrated in FIGS. 10A and B, respectively.
Figure 11B:
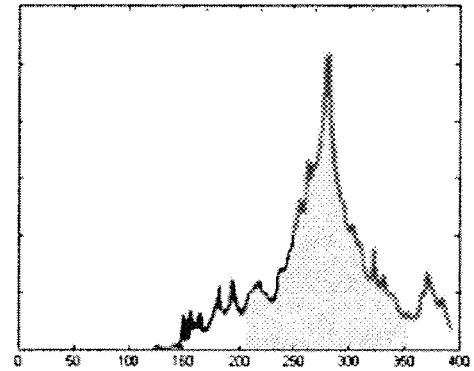

In process 48, the processor 26 detects the maximum likelihood as the position of the coil 16. The likelihood combinations from the different scales are combined, such as by summing. The sum provides a likelihood distribution of position. The sum is or is not weighted by scale, such as emphasizing smaller, middle, or larger scales. FIGS. 11A and B show two example combinations for high (FIG. 11A) and low (FIG. 11B) signal-to-noise ratios. In the examples of FIGS. 11A and B, the likelihood combinations shown in FIGS. 10A and B are combined. By combining, a robust detection of position is provided. The likelihood of the coil being at each position is provided by the distribution.

The maximum likelihood is given by the peak of the likelihood distribution. The position of the coil 16 is selected as the location for the peak. Other statistics may be used to select the position from the likelihood distribution. Using likelihood distributions for different axes, the position in an area or volume may be determined. Since likelihood is used based on multiple scales, the position determination may be more robust to noise and variation in coil geometry.

The position indicated by the maximum likelihood may be different than position indicated by the maximum signal (see FIG. 3B). The maximum signal is not the coil position, but is instead the position of anatomy. The maximum signal may also be susceptible to noise. Maximum likelihood may more consistently provide correct position even in light of noise and hardware variation. Since likelihood is used, additional information about the position is provided.

The position is used to indicate a position of the intervention device 24 on an image. The processor 26 converts the detected position into the coordinate system defined by the subject. The X, Y, and Z positions are originally in the coordinate system defined by the gradient coils 14. A geometric operation is performed to convert from one Cartesian coordinate system to another.

FIG. 1 shows one coil 16. In other embodiments, one or more additional coils 16 are provided. For example, coils 16 are spaced along part of a catheter. The coils 16 are used sequentially to determine position, resulting in positions for different parts of the catheter. Curve fitting to the positions may be used to determine the location along the entire part of the catheter.

The position may be used for purposes other than display. For example, the location is used to register a position of an image plane relative to a volume. As another example, the position is used for planning. The direction of travel of the interventional device 24 is determined and instructions are provided to avoid tissues or organs.

The likelihood distribution may also indicate confidence. The spread or distribution of the likelihood indicates the confidence. The distribution is measured from the maximum likelihood. For example, FIGS. 11A and B show the 90% confidence interval as the grey area under the likelihood distribution curve. For the high signal-to-noise ratio signal, the confidence is high as the confidence interval is narrow. For the lower signal-to-noise ratio signal, the confidence is lower as the confidence interval has a greater distribution.

The likelihood (e.g., magnitude of the maximum likelihood) and/or confidence information may be used other than for determining the position. Various further processes may use the information. For example, a filtering level is assigned based on the confidence level. Greater filtering may be applied for lesser likelihood or confidence. In another example, the likelihood or confidence is used in reconstruction. In yet another example, the likelihood or confidence is used for adding a graphic for the interventional instrument to an image. Where one or more of the coils may be unneeded, the coil or coils with the lesser confidence or likelihood are not used to determine overall position of the instrument. For curve fitting, the coil positions with the higher confidence or likelihood are more strongly weighted in the fitting than coil positions with lower confidence or likelihood. As another example, the instructions provided for intervention guidance are different depending on the likelihood and/or confidence.

The likelihood or confidence may be output to the user. A value, graph, image, or coloring is used to communicate the likelihood and/or confidence. This visual indication may allow the user to make decisions on whether, how, and/when to proceed with intervention. Different guidance approaches may be used depending on the confidence.

The memory 28 is a graphics processing memory, video random access memory, system memory, random access memory, cache memory, hard drive, optical media, magnetic media, flash drive, buffer, database, combinations thereof, or other now known or later developed memory device for storing data or video information. The memory 28 is part of an imaging system, part of a computer associated with the processor 26, part of a database, part of another system, a picture archival memory, or a standalone device.

The memory 28 stores K-space data, reconstructed projection data, and/or spectra. As an alternative or in addition, the memory 28 stores the likelihood parameters, modulus maxima, likelihood distribution, confidence, wavelets, scale information, parameter likelihoods, or other data being, to be, or already processed.

The memory 28 or other memory is alternatively or additionally a computer readable storage medium storing data representing instructions executable by the programmed processor 26 for localization of a coil for magnetic resonance (MR)-guided intervention. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

A display may be provided for indicating the position. The display is a monitor, LCD, projector, plasma display, CRT, printer, or other now known or later developed devise for outputting visual information. The display receives images, graphics, or other information from the processor 26 or memory 28.

One or more images representing a catheter position relative to a patient region are displayed. The image may be of a position, such as displaying coordinates. The image may be of a medical scan representing the region of the patient. For example, the position information is overlaid as a graphic on an image or images representing the patient. The position of the medical device is highlighted, marked by a graphic, or otherwise indicated on the image.

Figure 12:
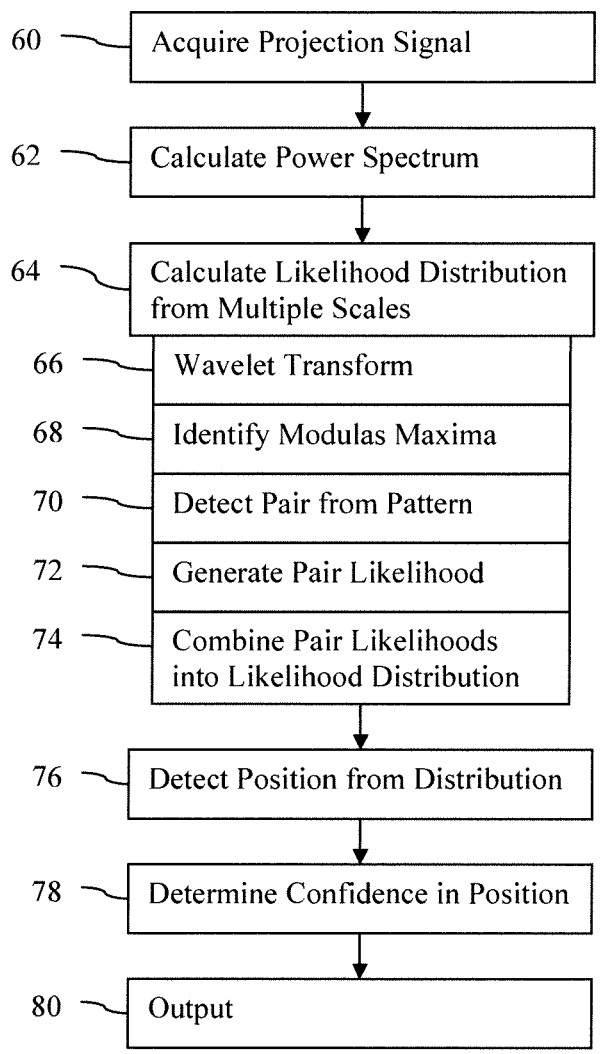
FIG. 12 is a flow chart diagram of an example embodiment of a method for localization of a coil for magnetic resonance (MR)-guided intervention.

FIG. 12 shows a method for localization of a coil for magnetic resonance (MR)-guided intervention. The method is performed by the MR system 10 of FIG. 1 or a different system using the process of FIG. 4 or a different process. The acts are performed in the order shown, but other orders may be provided. For example, act 78 is performed before act 76. Additional, different, or fewer acts may be provided. For example, acts 60 and 62 are performed separately and the earlier acquired data is later used to determine position in an independent method. As another example, acts 76, 78, and/or 80 are not performed.

In act 60, projections along one or more (e.g., three) spatial axes are acquired. The projections are acquired in real-time or as MR signals are received by the coil. The projections are formed within seconds or less after receipt of signals. The projections are acquired as K-space data.

The projections are acquired using a coil in a patient and connected to an interventional device. The interventional device is inserted within the patient or initially positioned adjacent to the patient in a known orientation. In response to an MR pulse, the coil within or by the patient receives signals. Due to the gradients, the signals are associated with a given axis. By repeating MR pulsing with different gradients, projections may be acquired along other dimensions.

In act 62, a power spectrum is calculated for each of the projections. An inverse Fourier transform is applied to the projection data. A power spectrum for each projection is provided where the intensity or power as a function of position along the frequency, and thus spatial axis, results. The power spectrum is calculated for each axis of interest.

In act 64, a likelihood distribution is calculated. The likelihood of the coil being at each of two or more different positions is determined. The distribution of the position of the coil may be used to find the position of the coil while also indicating other options. The confidence of the position, such as the magnitude of the likelihood and/or the deviation or other measure of the distribution of the likelihood may also be calculated.

Any acts for calculating likelihood distribution may be used. For example, training data of known positions with corresponding power spectra or other signals are used to train a machine-learnt algorithm (e.g., neural network, Bayes network, or other). Given an input feature set, such as the power spectra or characteristics derived from the power spectra, the machine-learnt algorithm outputs the likelihood distribution or position and corresponding likelihood.

In another embodiment represented in FIG. 12, acts 66-74 are performed. Additional, different, or fewer acts may be used. For example, individual transitions are used instead of pairs in act 70-74.

In act 66, a wavelet transform is performed. The power spectrum or other signal representing the response to an MR pulse at the coil as a function of space is transformed. The spatial domain signals are transformed. The signals along each axis of interest (e.g., X, Y, and Z) are transformed separately, but a combined transformation may be provided.

Any wavelet transformation may be used. The transformation decomposes the signal into a plurality of scales. Any number of scales may be used, such as two, three, four, five, six, or more. Any step size or distribution of scales may be used, such as dyadic scaling. The decomposition finds the first, second, or third derivative of the signal at different frequencies or other contribution. For each scale, a different frequency or range represented in the input signal is identified.

The likelihood distribution is estimated from results of the wavelet transforming. To estimate the likelihood distribution, the modulus maxima is identified in act 68. The modulus maxima represent sharp variations or transitions in the power spectrum. A positive or negative peak in the first or second derivative indicates a change in direction or transition. The modulus maxima are local extrema where the surrounding values are below the local extrema. Other peak or transition detection may be used.

The modulus maxima are found for each scale. None, one, or more modulus maxima may be identified for each scale. Since the response of the anatomy adjacent to the coil may produce a double humped or multiple transition signal, there are likely to be zero or an even number of modulus maxima for each scale. Due to noise, odd numbers may be provided.

In act 70, pairs of the modulus maxima are detected. Given the characteristic of the response (e.g., two peaks shown in FIG. 3B), pairs of modulus maxima indicate the coil. For other types of coils or response, other characteristics than pairing may be used.

The modulus maxima for each pair include a positive and a negative magnitude. Two positive or two negative modulus maxima are not paired. In other embodiments, other combinations of positive and negative are used.

The modulus maxima for each pair have signal symmetry. The magnitude of each pair is the same or sufficiently similar (i.e., within a threshold difference). Since the coil is surrounded by the same type of anatomy, the magnitudes of the pair should be equal or within a threshold of similarity. In other embodiments, other relationships than equal magnitude may be used, such as an order (e.g., high to low or low to high) and/or desired difference in magnitude.

The modulus maxima for each pair have a separation in distance that is proportional to the scale. The distance is based on the scale. Any threshold amount of variance from the distance may be used. In other embodiments, distance is used without proportionality to the scale.

The three characteristics are used in pairing. Any two modulus maxima satisfying the three criteria are identified as a candidate pair. A given modulus maxima may be part of more than one pair. Alternatively, the pairing that most satisfies the criteria is used. In other embodiments, one, two, or other number of characteristics is used. Additional, different, or fewer characteristics may be used.

The characteristics are used within each scale. The pairing in each scale is independent of the other scales. In alternative embodiments, the pairing in a given scale uses information from other scales. For example, the expected decay across scale is used. If the magnitude varies sufficiently from an empirical decay or from a decay calculated from all the modulus maxima, the modulus maxima or pair are removed from the list of candidates. Other characteristics than magnitude may be used for across scale comparison.

The characteristics are used to identify pairs satisfying one or more (e.g., all) of the thresholds for the characteristics. Any modulus maxima or possible pairs of modulus maxima not satisfying the criteria are discarded. The result is a list of candidate pairs of modulus maxima. These candidates represent possible positions of the coil.

In act 72, a pair distribution is assigned to each of the pairs. The likelihood of the coil being at a position in a range of locations about the pair is assigned. Any distribution function may be used. For example, a Gaussian function is assigned to represent the likelihood of position based on the pair. The variance and centering of the Gaussian or other function is based on the characteristics of the pair. For example, the center of the Gaussian is positioned at the center of the pair or offset from the center as a function of the scale. The variance is based on the magnitude of the pair. Other mappings of the pair distribution for each pair may be provided.

When only one pair is identified in a scale, that pair represents the entire contribution for the scale. The entire pair distribution is assigned to the pair. When no pair is identified in the scale, no pair distribution is assigned. When more than one pair is identified in the scale, the pair distributions are combined after weighting to account for the number of pairs.

Any weighting may be used. For example, the number of pairs is used to relatively weight the amplitudes of the pair distributions or to weight the amplitudes of the pair for assigning the distribution. As another example, the number of pairs in the scale, the amplitude of the pair, and the symmetry of the pair are used to weight.

The result is a collection of pair distributions representing likelihood for each scale. The pair distributions may or may not overlap with each other.

In act 74, the pair distributions from different scales are combined. The distribution for each scale may have a greater or lesser accuracy with corresponding lesser or greater susceptibility to noise. The combination across scales may have the benefits of both. Since likelihood distribution is used, the down sides of both are minimized or reduced.

Any combination may be used. In one embodiment, the likelihoods for each position are summed across scales. In other embodiments, an average, weighted average, or other function is used to combine.

The result is a likelihood distribution representing the chance that a coil is located at each of a plurality of different locations. The maximum likelihood represents the most likely location for the coil. Other positions may be more likely than yet others, but less likely than the maximum.

In act 76, a position of the coil is detected. The coil position is determined from the likelihood distribution. Any criteria may be used to select the position from the likelihood distribution. In one embodiment, the position with the maximum likelihood is selected from the likelihood distribution. Statistical or other approaches may be used. For example, a center location for a range of positions having a greater average or total likelihood than other ranges is selected. Any range size may be used.

By determining the position along each axis, the coordinates of the coil in one, two, or three dimensions is detected. For example, a three-dimensional position is based on locations indicated in the expected one-dimensional projection signals.

In act 78, a confidence is determined. The confidence is of the position. The confidence is determined from the likelihood distribution. For example, the magnitude of the maximum likelihood or other likelihood used to select the position indicates a confidence. In another example, the variance, deviation, or other statistical indication of likelihood distribution about the selected position is used to indicate the confidence. Other confidence calculations may be used. The confidence may be weighted by other criteria.

In act 80, the position, likelihood distribution, and/or confidence are output. The output is a display for the user. An image indicates the position of the coil or interventional device associated with the coil. The confidence may be indicated as a numerical value, color coding, or other information. The confidence may be used to determine options for intervention, given the anatomy involved.

In other embodiments, the output is to a process or processor. For example, different filtering is used in regions associated with the device than other regions in an image. This may allow highlighting the interventional device. As another example, instructions or recommendations for interventional options are output based on the position and/or confidence.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A system for localization of a coil for magnetic resonance (MR)-guided intervention, the system comprising:
   the coil;
   a medical device operable to be positioned within a patient, the coil connected with the medical device;
   an MR receiver connected with the coil; and
   a processor connected with the MR receiver, the processor configured to:
   (a) calculate X, Y, and Z data from information from the coil received in response to MR pulses, the X, Y, and Z data representing intensity as a function of spatial location along X, Y, and Z axes, respectively;
   (b) decompose the X, Y, and Z data into multiple scales; and
   (c) detect a position of the coil as a function of the decomposition and at least two transitions in the intensity in each of the X, Y, and Z axes.

2. The system of claim 1 wherein the medical device comprises a catheter and wherein the coil is positioned on a tip of the catheter.

3. The system of claim 1 wherein the medical device comprises a needle.

4. The system of claim 1 wherein the coil comprises a conductive coil.

5. The system of claim 4 wherein the conductive coil comprises a copper coil less than 4 mm in any direction.

6. The system of claim 1 wherein the processor is configured to decompose with a wavelet transform.

7. The system of claim 6 wherein the processor is configured to decompose with a dyadic wavelet transform.

8. The system of claim 1 wherein the processor is configured to calculate at least one modulus maximum for each of the multiple scales of each of the decomposed X, Y, and Z data.

9. The system of claim 8 wherein the processor is configured to detect, at each of the scales, pairs of the transitions from a symmetry of positive and negative magnitude of the corresponding modular maxima, a distance proportional to the scale, and a decay of the magnitude.

10. The system of claim 1 wherein the processor is configured to detect, at each of the scales, from an estimation of a parameter likelihood, the parameter likelihood for multiple pairs of the transitions at a same scale being divided as a function of a number of the pairs at the same scale, an amplitude of modulus maxima for the pairs, and a symmetry of the transitions of each pair.

11. The system of claim 1 wherein the processor is configured to detect the position from a sum of likelihoods from the multiple scales.

12. The system of claim 1 wherein the processor is further configured to calculate an indication of confidence of the position.

13. The system of claim 1 wherein the processor is configured to detect the position where the position of the coil corresponds to a different location than indicated by a maximum of the X, Y, and Z data.

14. A system for localization of a coil for magnetic resonance (MR)-guided intervention, the system comprising:
   the coil;
   a medical device operable to be positioned within a patient, the coil connected with the medical device;
   an MR receiver connected with the coil; and
   a processor connected with the MR receiver, the processor configured to:

(a) calculate X, Y, and Z data from information from the coil received in response to an MR pulse, the X, Y, and Z data representing intensity as a function of spatial location along X, Y, and Z axes, respectively;
(b) correlate the X, Y, and Z data with X, Y, and Z spectra models, respectively; and
(c) detect a position of the coil as a function of the correlations.

15. The system of claim 14 wherein the medical device comprises a catheter and wherein the coil is positioned on a tip of the catheter.

16. The system of claim 14 wherein the medical device comprises a needle.

17. The system of claim 14 wherein the coil comprises a conductive coil.

18. The system of claim 17 wherein the conductive coil comprises a copper coil less than 4 mm in any direction.

19. The system of claim 14 wherein the processor is configured to correlate by cross-correlation.

20. The system of claim 14 wherein the X, Y, and Z spectra models comprise expected one-dimensional projection signals.

21. The system of claim 14 wherein the coil comprises a solenoid coil.

* * * * *